(12) United States Patent
Holzer (10) Patent No.: US 10,188,272 B2
(45) Date of Patent: Jan. 29, 2019

(54) IMAGING CAPSULE (71) Applicant: Asher Holzer, Raanana (IL)

(72) Inventor: Asher Holzer, Raanana (IL)

(*) Notice: Subject to any disclaimer, the term of this patent is extended or adjusted under 35 U.S.C. 154(b) by 201 days.

(21) Appl. No.: 15/203,818

(22) Filed: Jul. 7, 2016

(65) Prior Publication Data

US 2018/0008130 A1 Jan. 11, 2018

(51) Int. Cl.
| A61B 1/00 | (2006.01) |
| A61B 1/06 | (2006.01) |
| A61B 1/018 | (2006.01) |
| A61B 1/04 | (2006.01) |
| A61B 34/00 | (2016.01) |
| A61B 90/00 | (2016.01) |
| A61B 1/31 | (2006.01) |
| A61B 34/30 | (2016.01) |
| A61B 17/00 | (2006.01) |

(52) U.S. Cl.
CPC ...... *A61B 1/00151* (2013.01); *A61B 1/00158* (2013.01); *A61B 1/018* (2013.01); *A61B 1/041* (2013.01); *A61B 1/0607* (2013.01); *A61B 1/31* (2013.01); *A61B 34/73* (2016.02); *A61B 90/361* (2016.02); *A61B 2017/00907* (2013.01); *A61B 2034/303* (2016.02); *A61B 2090/3966* (2016.02)

(58) Field of Classification Search
CPC . A61B 1/00151; A61B 1/00158; A61B 1/018; A61B 1/041; A61B 1/00082; F16L 55/26; F16L 55/256; F16L 55/30; F16L 55/32; F16L 55/34; G01N 21/954; A61M 25/0116; A61M 25/0119; A63H 11/00
USPC .................................................. 446/441, 443
See application file for complete search history.

(56) References Cited

U.S. PATENT DOCUMENTS

| 4,224,929 A * | 9/1980 | Furihata | A61B 1/00082 600/107 |
| 4,321,915 A | 3/1982 | Leighton et al. | |
| 6,485,409 B1 | 11/2002 | Voloshin et al. | |
| 7,056,283 B2 | 6/2006 | Baror et al. | |
| 2005/0272976 A1* | 12/2005 | Tanaka | A61B 1/00073 600/114 |
| 2006/0089533 A1* | 4/2006 | Ziegler | A61B 1/00156 600/114 |
| 2012/0029283 A1* | 2/2012 | Yamakawa | A61B 1/00154 600/114 |

* cited by examiner

*Primary Examiner* — Timothy J Neal
*Assistant Examiner* — Aaron B Fairchild
(74) *Attorney, Agent, or Firm* — D. Kligler IP Services Ltd.

(57) ABSTRACT

Described embodiments include a capsule, including a cyclically everting sleeve shaped to define a sleeve interior, a fluid, configured to facilitate the everting of the sleeve, contained within the sleeve interior, and a plurality of electrically-conductive coils coupled to the sleeve. The coils are configured to, when at least two of the coils are magnetized, advance the capsule within a lumen by applying an everting force to the sleeve. Other embodiments are also described.

28 Claims, 9 Drawing Sheets

IMAGING CAPSULE

FIELD OF THE INVENTION

Embodiments of the present invention relate to the field of medical devices, particularly to medical devices for facilitating procedures in the gastrointestinal (GI) tract.

BACKGROUND

Some applications call for imaging the GI tract from within the GI tract.

U.S. Pat. No. 6,485,409, whose disclosure is incorporated herein by reference, describes an endoscopic apparatus which advances within a lumen. The apparatus includes a probe having distal and proximal ends and a flexible sleeve coupled proximally to the probe. The sleeve is inflated in order to propel the probe within the lumen. The probe typically includes an imaging device, which captures images inside the lumen.

U.S. Pat. No. 7,056,283, whose disclosure is incorporated herein by reference, describes an endoscopic apparatus, including a probe having an anterior component and a posterior component, and a flexible dual-sleeved tube. The flexible dual-sleeved tube consists of a flexible external sleeve and a flexible internal sleeve within the external sleeve. The sleeves are coupled between the anterior component and the posterior component so as to define an enclosure between the sleeves, which enclosure is inflated in order to propel the anterior component within a lumen.

SUMMARY OF THE INVENTION

There is provided, in accordance with some embodiments of the present invention, a capsule, including a cyclically everting sleeve shaped to define a sleeve interior, a fluid, configured to facilitate the everting of the sleeve, contained within the sleeve interior, and a plurality of electrically-conductive coils coupled to the sleeve. The coils are configured to, when at least two of the coils are magnetized, advance the capsule within a lumen by applying an everting force to the sleeve.

In some embodiments, the coils are radiopaque.

In some embodiments, the capsule further includes one or more imaging devices contained within the sleeve interior and configured to image an interior of the lumen.

In some embodiments, a surface of the everting sleeve is transparent.

In some embodiments, the fluid includes a mixture of alcohol and water.

In some embodiments, at least one of the coils is a barrel coil.

In some embodiments, the capsule further includes a ferromagnetic material disposed within a lumen of the barrel coil.

In some embodiments, at least some of the coils overlap each other.

In some embodiments, the coils are arranged in a plurality of rings running longitudinally along the sleeve.

In some embodiments, the coils are arranged in four or more rings distributed along a circumference of the sleeve.

In some embodiments, the capsule further includes respective conducting elements attached to each coil of the coils, the respective conducting elements being configured to magnetize the coil by passing an electric current between the coil and an exterior of the lumen.

In some embodiments, a diameter of the sleeve is adjustable between a lower limit and an upper limit.

In some embodiments, the capsule further includes a net configured to hold the diameter of the sleeve at the upper limit.

In some embodiments, the capsule further includes one or more fiducial markers on the sleeve.

In some embodiments, the capsule further includes one or more location sensors coupled to the sleeve, configured to transmit a signal indicative of a location and an orientation of the capsule.

There is further provided, in accordance with some embodiments of the present invention, a method that includes inserting a capsule, which includes a cyclically everting sleeve shaped to define a sleeve interior that contains a fluid, entirely into a lumen. The method further includes advancing the capsule within the lumen, by applying an everting force to the sleeve.

In some embodiments, the capsule includes a plurality of electrically-conductive coils coupled to the sleeve, and applying the everting force to the sleeve includes applying the everting force to the sleeve by alternatingly magnetizing respective subsets of the coils.

In some embodiments, alternatingly magnetizing the respective subsets of the coils includes magnetizing two of the coils that are opposite one another such that the two coils attract one another.

In some embodiments, alternatingly magnetizing the respective subsets of the coils further includes magnetizing another two of the coils that are opposite one another such that the two coils repel one another.

In some embodiments, alternatingly magnetizing the respective subsets of the coils includes alternatingly magnetizing the respective subsets of the coils in a predetermined order that is based on respective longitudinal positions of the coils along the sleeve.

In some embodiments, the method further includes, by imaging the coils while the capsule is inside the lumen, repeatedly identifying which ones of the coils are at a longitudinal end of the sleeve, and alternatingly magnetizing the respective subsets of the coils includes alternatingly magnetizing the respective subsets of the coils in response to the identifying.

In some embodiments, alternatingly magnetizing the respective subsets of the coils includes, in response to the capsule reaching a bend in the lumen, magnetizing a subset that includes coils that are located at different circumferential positions along the sleeve, relative to circumferential positions of coils belonging to the subset that was most recently magnetized.

In some embodiments, the method further includes ascertaining that the capsule has reached the bend, in response to imaging one or more fiducial markers on the sleeve.

In some embodiments, the capsule includes one or more location sensors, and the method further includes ascertaining that the capsule has reached the bend, in response to a signal from the sensors.

In some embodiments, applying the everting force to the sleeve includes applying the everting force to the sleeve by directing a stream of fluid at the sleeve.

In some embodiments, the lumen is a gastrointestinal lumen of a subject.

In some embodiments, the method further includes, while the capsule is inside the lumen, adjusting a diameter of the sleeve in response to the capsule reaching a portion of the lumen at which a diameter of the lumen changes.

In some embodiments, adjusting the diameter of the sleeve includes increasing the diameter of the sleeve by heating the fluid.

There is further provided, in accordance with some embodiments of the present invention, a method that includes inserting a cyclically everting sleeve entirely into a lumen, and, subsequently, advancing a tool through the lumen, by passing the tool through the sleeve.

The present invention will be more fully understood from the following detailed description of embodiments thereof, taken together with the drawings, in which:

DETAILED DESCRIPTION OF EMBODIMENTS

Overview

Maneuvering imaging apparatus within an intestine, particularly the large intestine, poses several challenges. For example, friction between the imaging apparatus and the inner wall of the intestine should be minimized to the extent possible, in order not to overly stress the inner wall of the intestine. Also, due to the tortuosity of the intestine, the imaging apparatus should be capable of turning corners smoothly, without puncturing the intestinal wall at any point.

Embodiments described herein addresses these challenges, by providing an imaging capsule that may be inserted into the intestine of a subject, and then navigated from outside of the subject. The capsule comprises a cyclically everting sleeve, typically having a smooth exterior, which may be advanced within the intestine by the application of an everting force, such as a squeezing force applied to one end of the sleeve. For example, a plurality of electrically-conductive coils coupled to the sleeve may be alternatingly magnetized, such as to apply a near-continuous everting force that propels the capsule forward. The sleeve typically contains one or more imaging devices, which image the interior of the intestine as the capsule moves.

Since the capsule moves by eversion—rather than by simply sliding through the intestine—there is a relatively small amount of friction between the capsule and the inner wall of the intestine. The smoothness of the capsule may further reduce friction between the capsule and the inner wall, and may also help prevent any punctures from occurring. (Aside from increased safety, a further advantage of reduced friction is a reduced amount of power required to move the capsule within the intestine.) Moreover, the capsule is flexible, and can thus easily navigate the twists and turns of the intestinal track.

More generally, the capsule described herein may be used for navigating any lumen, including, for example, the lumen of a pipe. Moreover, the capsule described herein may be used even for non-imaging applications. For example, the capsule may be used to deliver a particular substance, such as a medication, to a site within the intestine. In yet other embodiments, the capsule may be used as a low-friction conduit for a tool, such as an endoscope.

Apparatus Description

Figure 1:
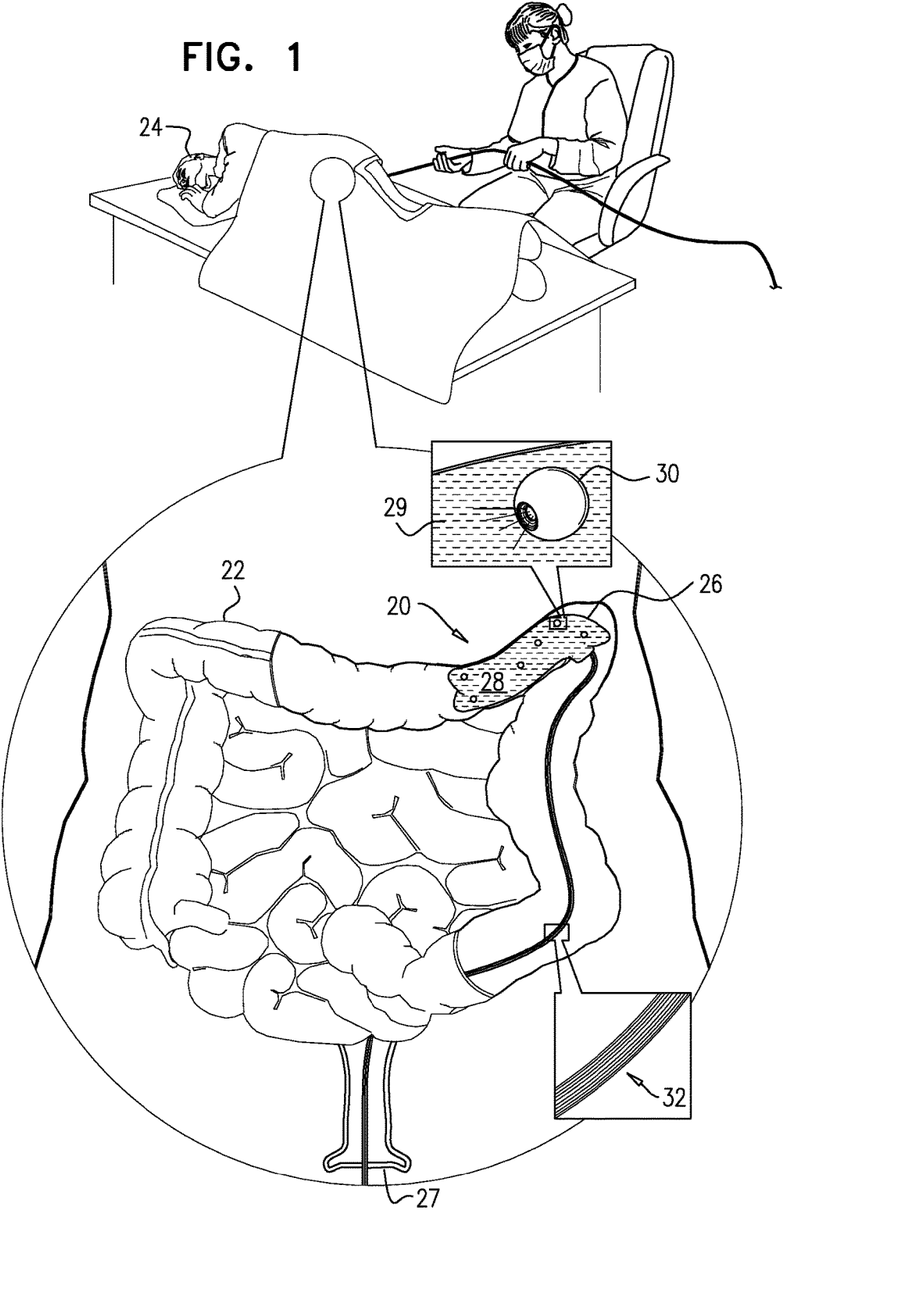
FIG. 1 is a schematic illustration of an imaging capsule within an intestinal lumen, in accordance with some embodiments of the present invention.

Reference is initially made to FIG. 1, which is a schematic illustration of an imaging capsule 20 within an intestinal lumen, in accordance with some embodiments of the present invention. Capsule 20 may be inserted, for example, into the lumen of an intestine 22 of a subject 24, e.g., through the anus 27 of the subject.

As further described below, capsule 20 comprises a cyclically everting sleeve 26, such that the capsule may be advanced within the lumen by applying an everting force to the sleeve. In the context of the present application, including the claims, the term "cyclically everting" means that the sleeve is capable of everting (i.e., turning inside out) over many cycles of eversion, e.g., over an infinite number of cycles. The sleeve is shaped to define a sleeve interior 28 that contains a fluid 29, which facilitates eversion of the sleeve. Typically, one or more imaging devices 30 are disposed within the sleeve interior; for example, imaging devices 30 may be suspended in fluid 29, inside sleeve interior 28. As the capsule advances within the lumen, the imaging devices image the interior of the lumen.

In general, the imaging devices may be of any suitable type. In some embodiments, a Given Imaging PillCam® product is used for each of the imaging devices. Typically, each of the imaging devices comprises a light source, such as an annular light source, that facilitates the imaging by the imaging device by providing light for the imaging device. Alternatively or additionally, sleeve interior 28 may contain one or more light sources that are separate from the imaging devices.

FIG. 1 shows a plurality of conducting elements (e.g., wires) 32 emerging from the sleeve and extending out of anus 27. Conducting elements 32—which are connected to a current source or voltage source (not shown) outside of the lumen—facilitate the conduction of electricity to and from the capsule, such as to advance capsule 20 within the intestine. For example, as further described below with reference to FIG. 3, capsule 20 may comprise a plurality of coils, and conducting elements 32 may connect to the coils such as to form a plurality of circuits. By passing electric currents along these circuits, the capsule is advanced.

Figure 2:
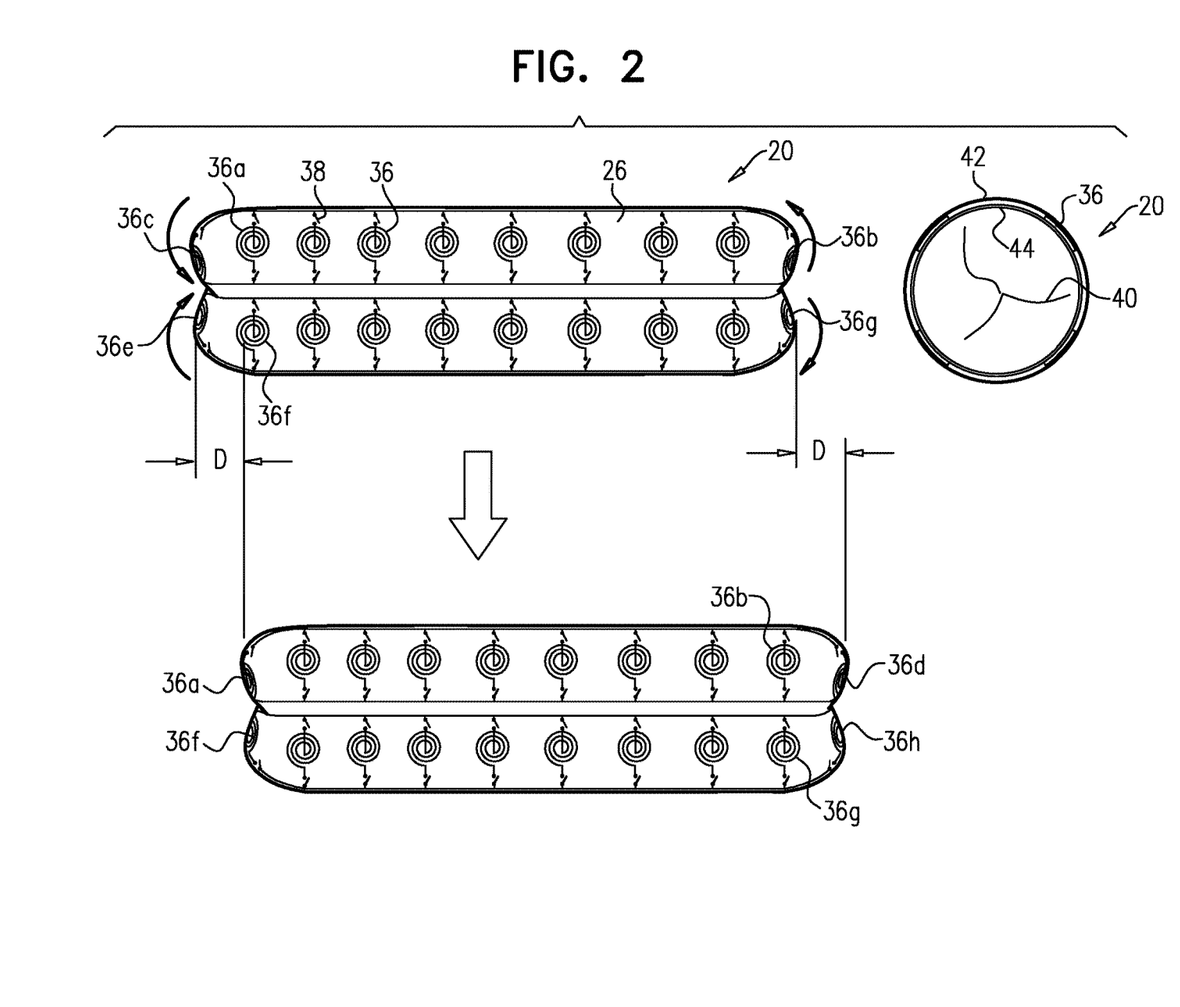
FIG. 2 is a schematic illustration of a capsule, in accordance with some embodiments of the present invention.
Figure 3:
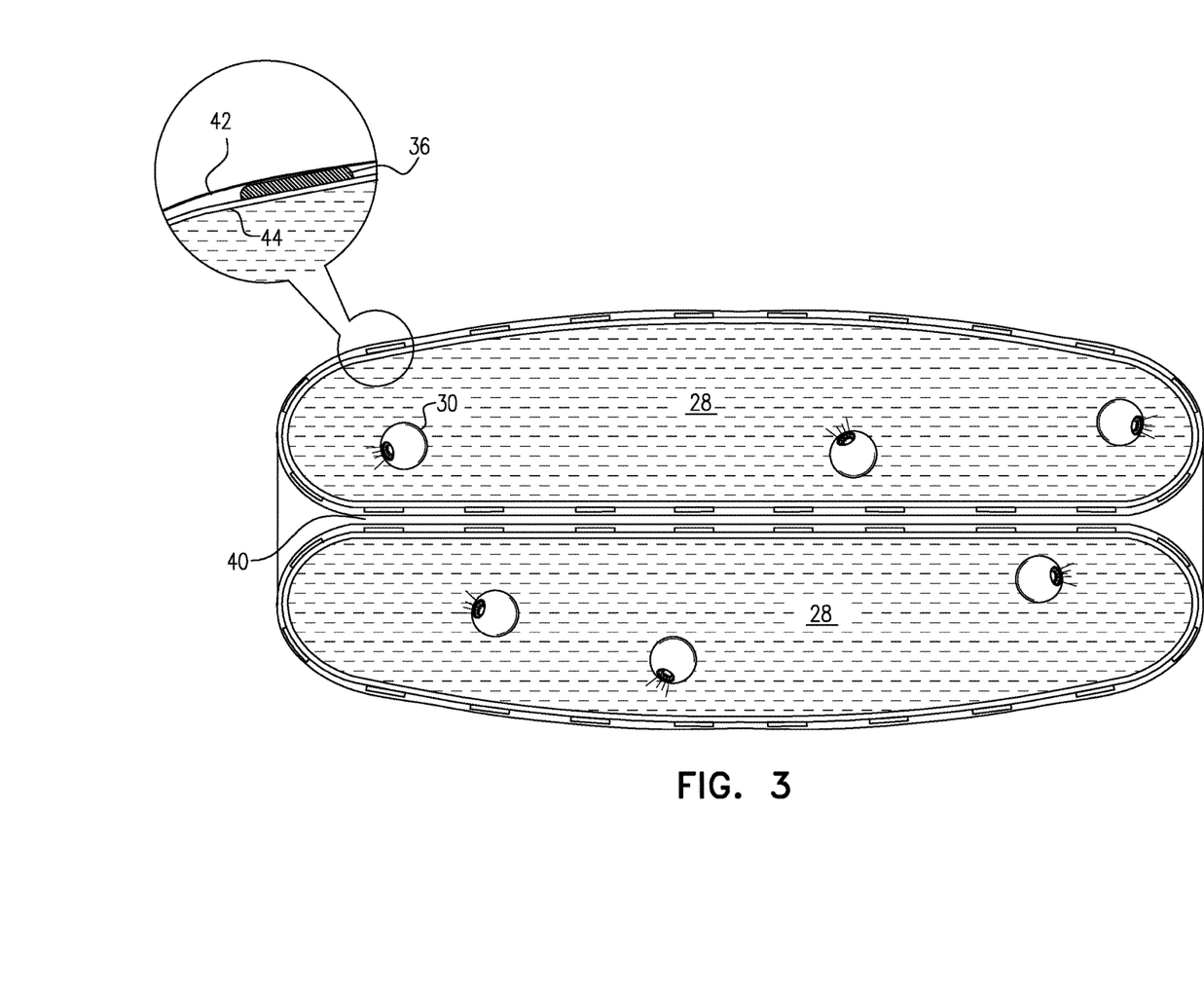
FIGS. 3-4 are schematic illustrations of longitudinal cross-sections of a capsule, in accordance with some embodiments of the present invention.

Reference is now made to FIG. 2, which is a schematic illustration of capsule 20, in accordance with some embodiments of the present invention. FIG. 2 includes longitudinal views, and a transverse cross-sectional view, of the capsule. Reference is further made to FIG. 3, which is a schematic illustration of a longitudinal cross-section of the capsule, in accordance with some embodiments of the present invention.

In the embodiment of FIGS. 2-3, capsule 20 comprises a plurality of electrically-conductive coils 36 coupled to sleeve 26, which, as further described below, may be magnetized such as to move the capsule within the lumen. In some embodiments, the coils are arranged in a plurality of rings (e.g., four or more rings) running longitudinally along the sleeve; these rings may, for example, be distributed along the circumference of the sleeve. For example, the transverse cross-sectional view of FIG. 2 shows four rings of coils distributed around the circumference of the sleeve (at approximately "1:30," "4:30," "7:30," and "10:30"). Each of the longitudinal views of FIG. 2 shows the respective exposed portions of two neighboring rings (e.g., the "1:30" and "4:30" rings) of the four rings, while FIG. 3 shows two opposite rings (e.g., the "1:30" and "7:30" rings) of the four rings. (In general, notwithstanding the specific embodiments shown in the figures, it is noted that coils 36 may be arranged in any suitable arrangement along the sleeve.)

The bottom longitudinal view in FIG. 2 shows the capsule advanced a distance D with respect to the top longitudinal view. (The exact manner in which the capsule is advanced is described with reference to subsequent figures.) As noted above, the capsule advances via eversion of the sleeve, such that the bottom longitudinal view differs from the top longitudinal view as follows:

(i) In the top longitudinal view, coils 36c and 36e are at the proximal end of the sleeve, and are beginning to enter the sleeve lumen 40 of the sleeve. Conversely, coils 36b and 36g are at the distal end of the sleeve, and have almost completely emerged from sleeve lumen 40 of the sleeve. Coils 36a and 36f are near the proximal end of the sleeve.

(ii) In the bottom longitudinal view, due to eversion of the sleeve, coils 36c and 36e have entered the sleeve lumen of the sleeve, and have thus disappeared from view, while coils 36a and 36f have reached the proximal end of the sleeve. Coils 36b and 36g have moved proximally, while coils 36d and 36h have emerged from inside the sleeve lumen.

In some embodiments, a respective pair of conducting elements 32 is connected to each coil (one conducting element being connected to each end of the coil), such that, for example, if capsule 20 comprises N coils, capsule 20 will comprise 2N conducting elements. In other embodiments, e.g., as shown in FIG. 2, multiplexing is used, such that a single conducting element 32 is connectable to multiple ones of the coils. (So as not to overly complicate the figure, the extensions of the conducting elements from the sleeve are not shown.) For example, as shown in FIG. 2, each ring of coils may be connectable to a respective pair of conducting elements. To connect a particular coil to the relevant conducting elements, and thus form a circuit, the switches 38 between the coil and the conducting elements are closed. In general, switches 38 may be controlled remotely from the outside the body of the subject, via any suitable remote-control technique.

In some embodiments, the surface 44 of the sleeve upon which the coils are disposed is transparent, such that light can pass through surface 44 to the imaging devices within the sleeve interior. Typically, surface 44 is an inner surface of the sleeve, and the sleeve further comprises an outer surface 42, which, typically, is also transparent. By covering the coils, the outer surface provides the sleeve with a smooth exterior, such that the sleeve does not damage the inner intestinal wall. Typically, as shown in FIG. 3, a fluid, such as a gel, separates between the inner and outer surfaces of the sleeve. In some embodiments, the inner and outer surfaces are joined together by a string and/or other fastener. In any case, as the sleeve everts, the inner and outer surfaces typically move in unison, i.e., one of the surfaces does not move relative to the other. (Thus, the inner and outer surfaces may be collectively referred to as a "double wall" or "double surface.")

Figure 4:
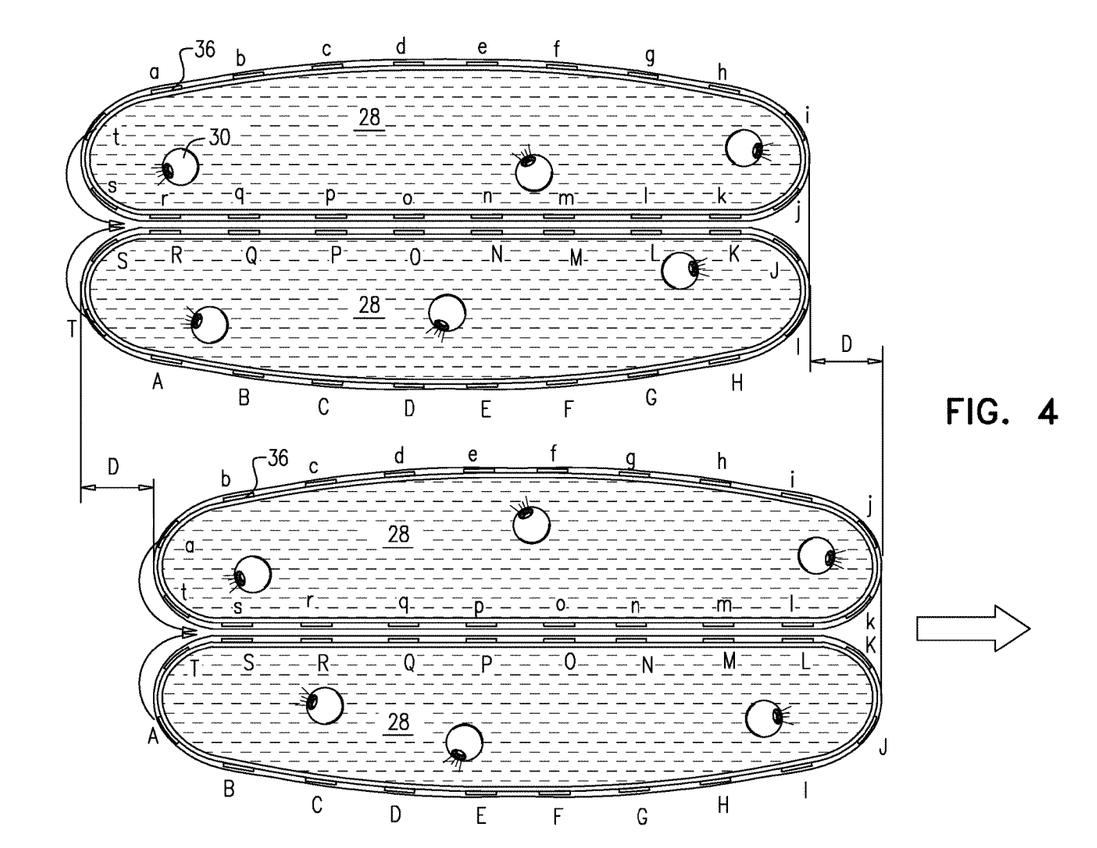

Reference is now made to FIG. 4, which is a schematic illustration of longitudinal cross-sections of the capsule, in accordance with some embodiments of the present invention. As in FIG. 3, each of the longitudinal cross-sectional views in FIG. 4 shows two opposite rings of coils. As in FIG. 2, the bottom longitudinal cross-sectional view in FIG. 4 shows the capsule advanced a distance D, relative to the top longitudinal cross-sectional view.

FIG. 4 illustrates that an everting force may be continually (e.g., continuously, or near-continuously) applied to the sleeve—thus advancing the capsule within the lumen—by alternatingly magnetizing respective subsets of the coils, such as by alternatingly magnetizing respective pairs of opposite coils, such that the two coils of each pair attract one another. For example, in the top view, opposite coils "t" and "T" are magnetized by passing a current through the coils (via the conducting elements described earlier), such that coils "t" and "T" attract one another. The "t-to-T" attraction exerts an everting force on the sleeve, causing the sleeve to evert, such that the capsule moves forward by a distance D. Subsequently, as shown in the bottom view, opposite coils "a" and "A" are magnetized, such that the sleeve again everts, and the capsule again moves forward by a distance D. Subsequently, coils "b" and "B" may be magnetized, and so on. In this manner—i.e., by continually magnetizing a pair of opposite coils that is near the proximal end of the sleeve, such as the proximal most pair of coils—the capsule may be advanced within the lumen.

Depending on the current position and orientation of the capsule, one pair of rings might be better positioned for advancing the capsule than another pair of rings. For example, upon the capsule reaching a bend in the lumen, the rings of coils that were most recently magnetized might not be able to apply the everting force necessary for navigating the bend, and therefore, a different pair of rings may be magnetized instead. For example, with reference again to the transverse cross-section of FIG. 2, the "1:30" and "7:30" rings might be used to advance the capsule up to the bend. Subsequently, instead of magnetizing a pair of coils from the "1:30" and "7:30" rings to navigate the bend, a pair of coils from the "4:30" and 10:30" rings may be magnetized.

In some embodiments, the capsule comprises one or more fiducial markers (e.g., radiopaque fiducial markers), which are disposed on the everting sleeve. By imaging the sleeve, and ascertaining the orientations of the markers, and/or the positions of the markers relative to each other, it may be ascertained that the capsule has reached a bend. Consequently, a different pair of rings may be used to advance the capsule past the bend, as described above. Alternatively or additionally, the capsule may include one or more location sensors, which may, for example, be coupled to the sleeve. Such location sensors may be configured to (collectively) transmit a signal indicative of the location and orientation of the capsule, such that, based on the signal, it may be ascertained that the capsule has reached a bend in the lumen.

In some embodiments, a radiopaque material, such as barium, is contained inside sleeve interior 28. Such a radiopaque material may facilitate fluoroscopic imaging of the sleeve, such as to further facilitate advancement of the sleeve.

In some cases, by imaging the fiducial markers on the sleeve, and/or by imaging the coils, it may be ascertained that the capsule is not moving. In response thereto, a different pair of rings may be tried, until the capsule resumes its movement.

In some cases, more than one pair of coils may be magnetized at a time. For example, with reference to the top view of FIG. 4, coils "s" and "S" may magnetized, such that these coils attract one another, for at least part of the time that coils "t" and "T" are magnetized. The "s-to-S" attraction may provide some additional everting force that propels the capsule forward. Alternatively or additionally, coils "j" and "J" may be magnetized such that these coils repel one another, and/or coils "i" and "I" may be magnetized such that these coils repel one another, in order to provide additional everting force. Alternatively or additionally, for embodiments having more than two rings of coils (such as the four-ring embodiment shown in FIG. 2), a pair of coils from a second pair of rings may also be magnetized. For example, assuming that FIG. 4 shows the "1:30" and "7:30" rings from FIG. 2, a second pair of coils—one coil being near the proximal end of the "4:30" ring, and the other coil being near the proximal end of the "10:30" ring—may be magnetized for at least part of the time during which coils "t" and "T" are magnetized, such as to create an additional everting force.

In some cases, the subsets of the coils are alternatingly magnetized in a predetermined order that is based on the respective longitudinal positions of the coils along the sleeve. For example, with reference to FIG. 4, the predetermined order may be "a-A," "b-B," "c-C," etc. In other cases, however, the movement of the capsule within the lumen may be unpredictable, such that the positions of the coils are not necessarily as expected. Hence, in some embodiments, the coils are imaged while the capsule is inside the lumen. At each movement step, the image of the coils is used to identify which ones of the coils are at the longitudinal end of the sleeve, and the identified coils are then magnetized. Thus, for example, with reference to the top view in FIG. 4, it may be identified that coils "t" and "T" are at the proximal end of the sleeve, and therefore, coils "t" and "T" may be magnetized.

In some embodiments, the coils are radiopaque, such that the coils may be fluoroscopically imaged. For example, each one of the coils may comprise a radiopaque marker, at least some of the radiopaque markers differing from each other in form, such that the respective positions of the coils may be ascertained from the images.

As depicted in FIG. 4, in some embodiments, due to motion of the capsule, imaging devices 30 freely move within sleeve interior 28, and/or change their orientation. Such movement and/or change in orientation of the imaging devices may provide greater coverage of the intestinal interior. Alternatively or additionally, the respective positions and/or orientations of the imaging devices may be remotely controlled.

Figure 5:
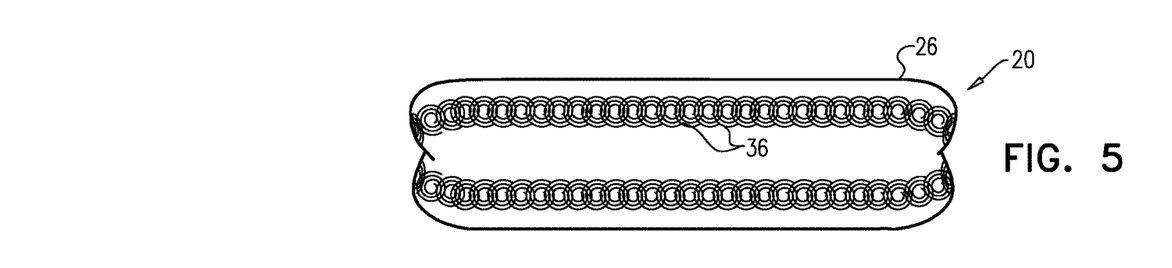
FIG. 5 is a schematic illustration of a capsule, in accordance with some embodiments of the present invention.

Reference is now made to FIG. 5, which is a schematic illustration of capsule 20, in accordance with some embodiments of the present invention.

A challenge in navigating the capsule is that, at times, it is possible that no pair of coils will be suitably positioned. For example, if no pair of coils is positioned near the longitudinal end of the sleeve, the capsule might become stuck. To address this challenge, in some embodiments, at least some of coils 36 overlap each other, such that gaps between the coils are reduced or eliminated. Alternatively, even if the coils do not overlap, they may be placed contiguously, i.e., in contact with each other.

For example, FIG. 5 shows an embodiment in which each coil overlaps with its two longitudinal neighbors, such that the everting sleeve is covered by rings of longitudinally overlapping coils. (For simplicity, FIG. 5 omits the conducting elements.) Alternatively or additionally to longitudinally overlapping, the coils may overlap (or, at least, be contiguous) circumferentially. That is, the everting sleeve may be covered by overlapping (or contiguous) rings of coils. For example, with reference again to the transverse cross-section of FIG. 2, a ring of coils may be positioned at each of 12:00, 1:00, 2:00, etc.

Figure 6A:
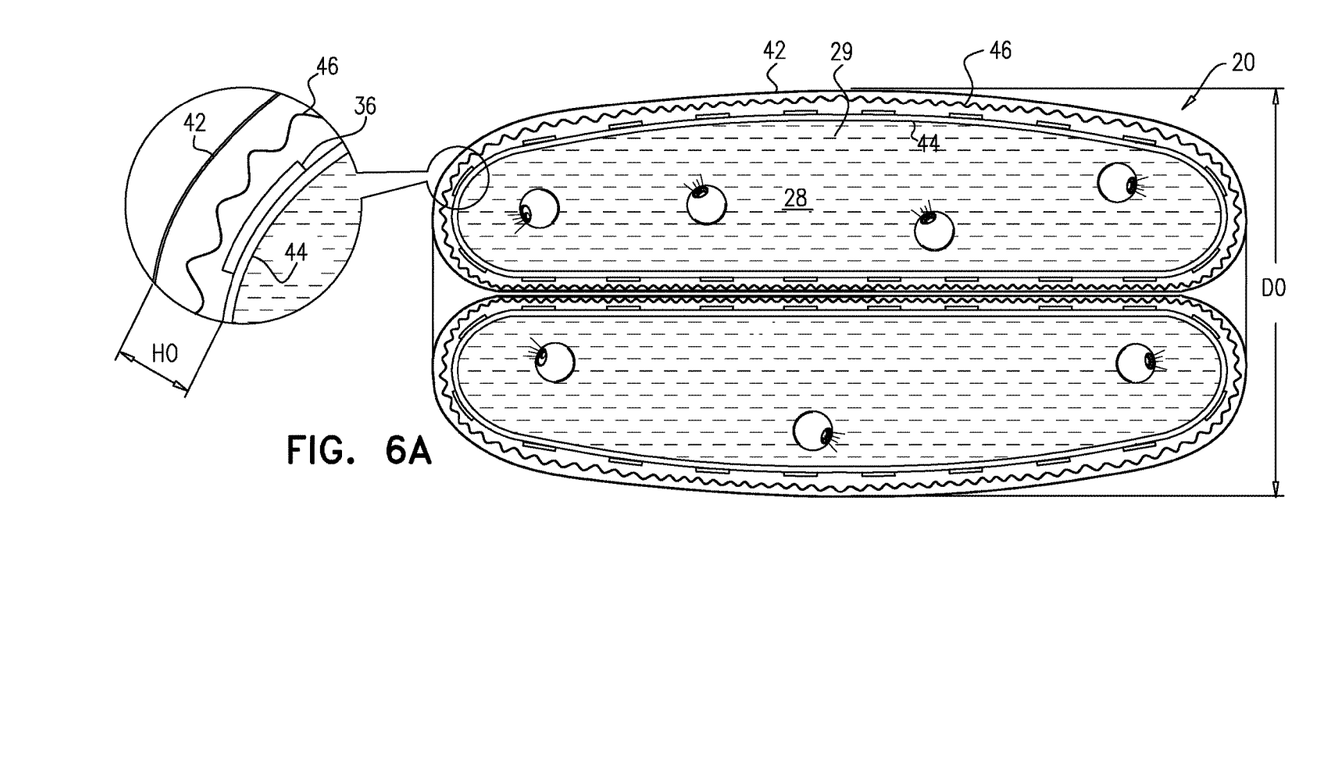
FIGS. 6A-C and 7 are schematic illustrations of longitudinal cross-sections of a capsule, in accordance with some embodiments of the present invention.
Figure 6B:
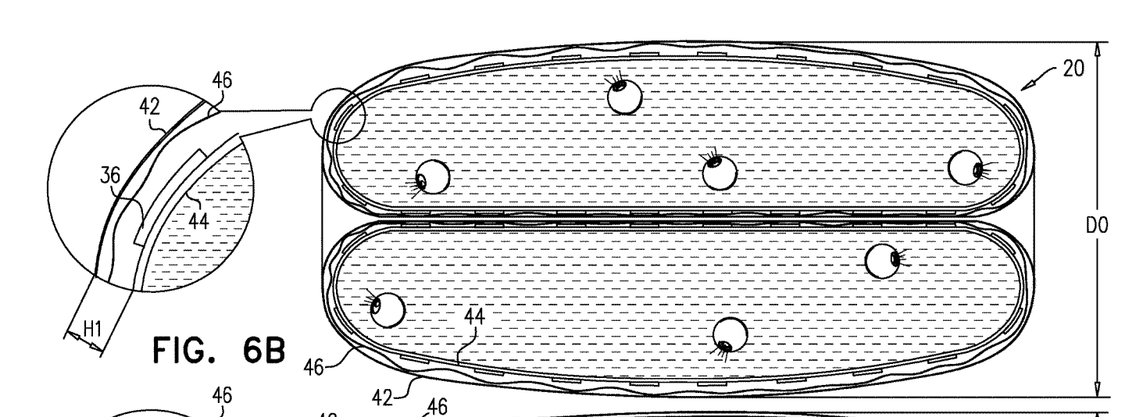
Figure 6C:
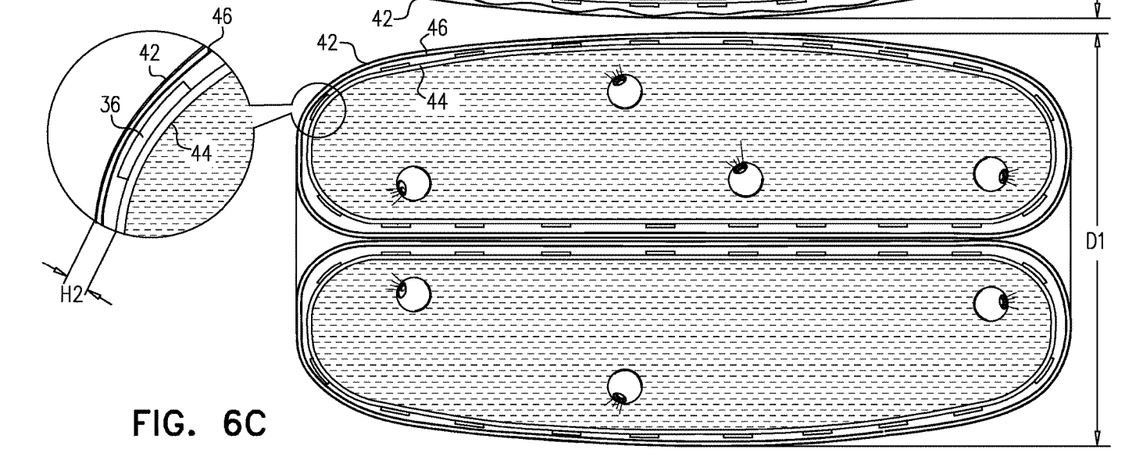

Reference is now made to FIGS. 6A-C, which are schematic illustrations of longitudinal cross-sections of capsule 20, in accordance with some embodiments of the present invention.

Typically, to move effectively through the lumen, the diameter of the sleeve must be approximately equal to that of the lumen, in order to maintain a minimum amount of radial force between sleeve 26 and the wall that surrounds the lumen. (In other words, the sleeve must be "squeezed" by the lumen.) Hence, if the diameter of the sleeve were constant, the sleeve might be suitable only for a narrow range of lumen diameters. For example, although the intestinal lumen is normally collapsed, there may be portions of the lumen that are expanded. If the sleeve were not capable of expanding to the diameter of these expanded portions, the sleeve might not be able to pass through these portions.

Hence, the embodiment of FIGS. 6A-C provides an adjustable sleeve diameter. Thus, for example, the embodiment of FIGS. 6A-C is suitable for lumens having a non-constant diameter, in that, upon the capsule reaching a portion of the lumen at which the diameter of the lumen changes, the diameter of the sleeve may be appropriately adjusted.

In some embodiments, the diameter of the sleeve is adjusted by changing the temperature of fluid 29 inside sleeve interior 28. For example, the diameter of the sleeve may be increased by heating fluid 29, e.g., by subjecting the fluid to an alternating radiofrequency (RF) energy field. In some embodiments, fluid 29 comprises a mixture of alcohol and water. As the fluid is heated past the boiling temperature of the alcohol (e.g., 42 degrees centigrade), bubbles of gaseous alcohol are formed. These bubbles cause the volume of the sleeve interior to increase, thus increasing the diameter of the sleeve. In some embodiments, alcohol-containing balloons are suspended in fluid 29. As the alcohol within the balloons boils, the balloons expand, thus increasing the diameter of the sleeve.

Typically, to facilitate the expansion of the sleeve, inner surface 44 of the sleeve, and outer surface 42 of the sleeve, are made of a compliant material. To prevent the sleeve from excessively expanding (and thus causing the inner surface and/or outer surface to tear, and/or causing damage to the lumen within which the capsule is situated), some embodiments provide a net 46, which is configured to hold the diameter of the sleeve at an upper limit D1, i.e., net 46 prevents expansion of the sleeve beyond diameter D1. Net 46 is typically situated between the inner and outer surfaces; for example, net 46 may be suspended in a compressible gel that separates between the surfaces. (As the sleeve everts, net 46 typically moves in unison with the inner and outer surfaces.) Net 46 may be manufactured, for example, of a metallic material, or any other non-compliant material. (As described below, the net "expands" by virtue of a reduction in slack in the net, not due to any stretching of the net.)

FIGS. 6A-C illustrate expansion of the sleeve, and the functioning of net 46, as follows:

(i) FIG. 6A shows the sleeve at a base diameter D0, which the sleeve maintains at normal body temperature and pressure. (D0 is, under normal conditions, the lower limit for the diameter of the sleeve.) At base diameter D0, net 46 is fully slacked, and the distance between inner surface 44 and outer surface 42 is at a base value H0.

(ii) FIG. 6B shows the sleeve interior beginning to expand. Outward expansion of inner surface 44 has caused compression of the gel that separates between the inner and outer surfaces, such that the distance between the surfaces has decreased to H1. As a further result of the outward expansion of inner surface 44, the slack in net 46 has decreased, such that the diameter of the net has increased. As inner surface 44 continues to expand, an outward expansionary force is exerted on outer surface 42, and the outer surface, also, begins to expand.

(iii) FIG. 6C shows outer surface 42 expanded to the full extent allowed by net 46. At this stage, the diameter of the outer surface (and of the sleeve) is at an upper limit D1, and the distance between the surfaces is at a minimum value H2. Due to being taut (and hence, fully expanded), the net prevents the inner surface (and hence, the outer surface) from expanding any further.

Figure 7:
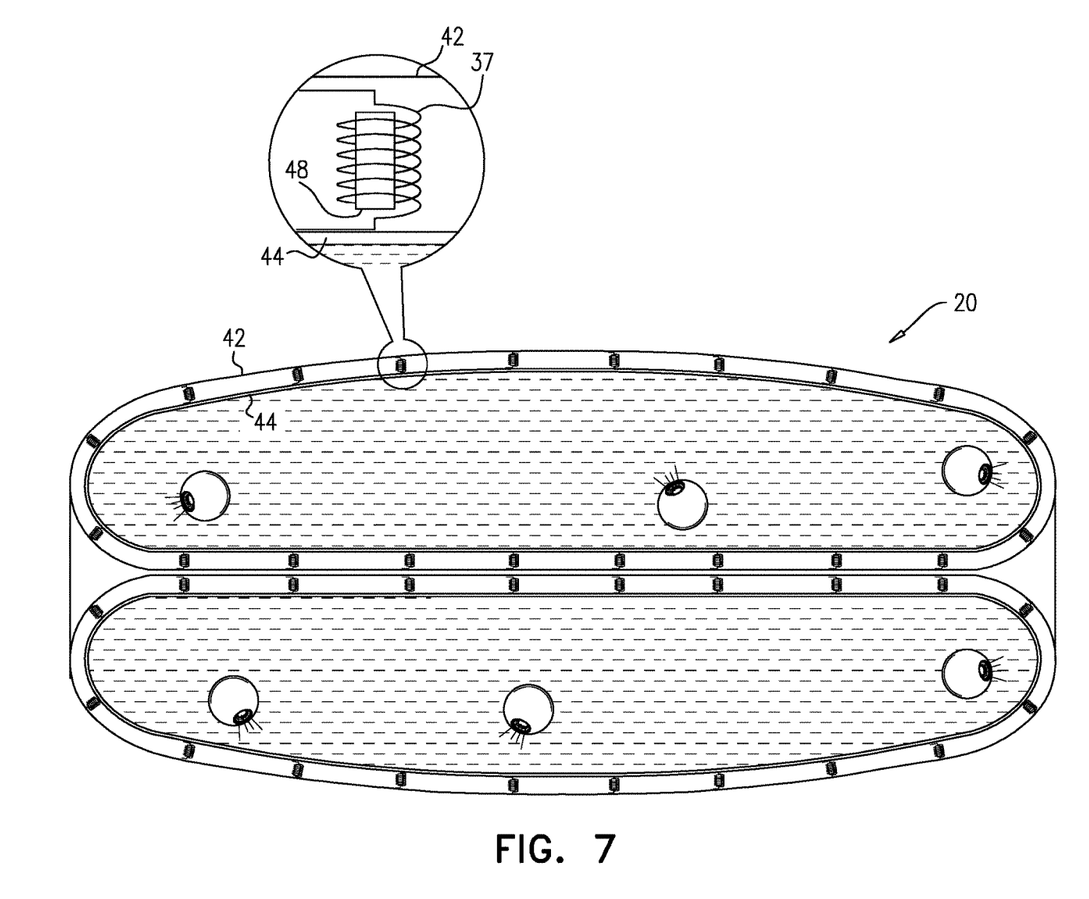

Reference is now made to FIG. 7, which is a schematic illustration of a longitudinal cross-section of capsule 20, in accordance with some embodiments of the present invention.

As opposed to showing the flat coils 36 shown in previous figures, FIG. 7 shows barrel coils 37, which may, upon being magnetized, provide greater everting force than flat coils 36. In some embodiments, the everting force is increased even further, by the disposition of a ferromagnetic material, such as a ferrite core 48, within the lumen of at least one of the barrel coils. For example, as shown in the figure, a respective ferrite core 48 may be suspended in the gel that separates between inner surface 44 and outer surface 42, within the lumen of each one of barrel coils 37. (For simplicity, the conducting elements connecting the barrel coils to the voltage or current source are not shown.)

Figure 8:
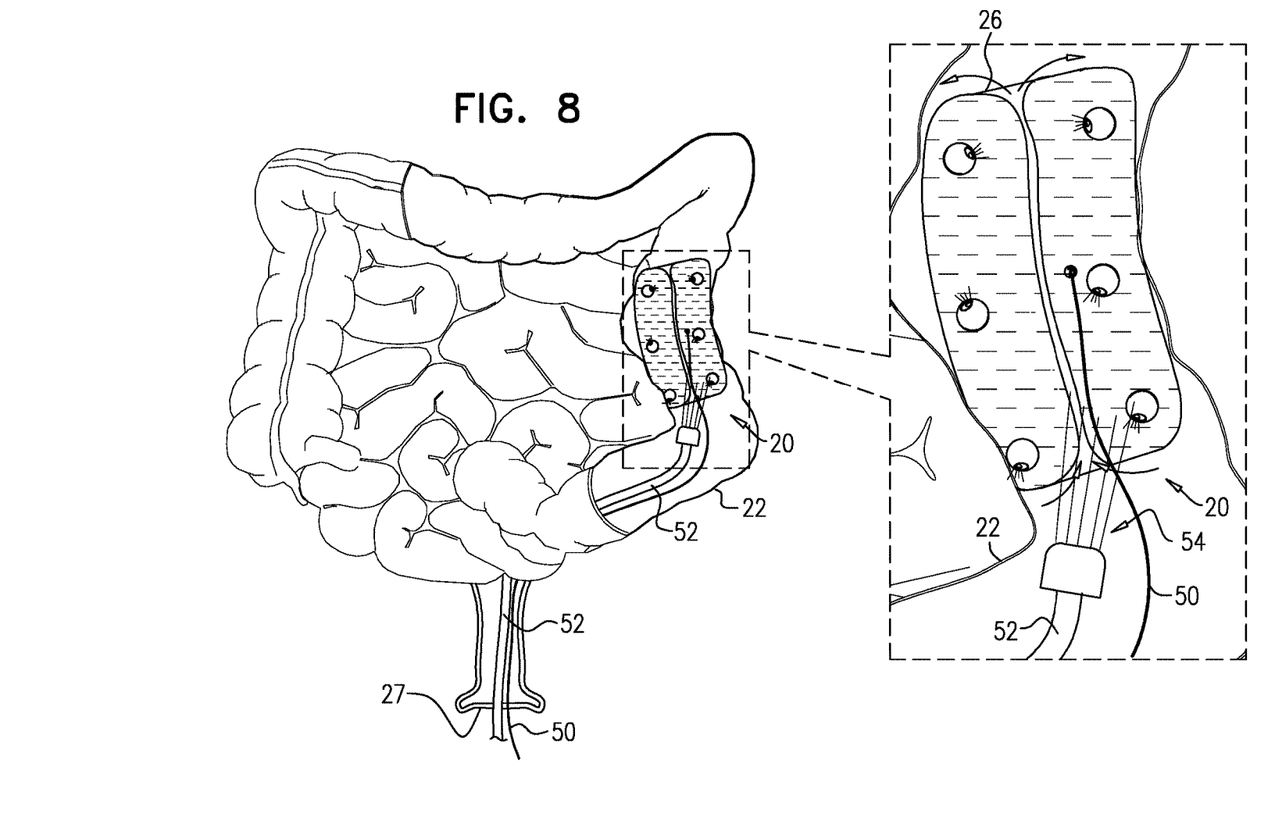
FIG. 8 is a schematic illustration of a capsule within the lumen of an intestine, in accordance with some embodiments of the present invention.

Reference is now made to FIG. 8, which is a schematic illustration of capsule 20 within the lumen of an intestine 22, in accordance with some embodiments of the present invention.

In some embodiments, as shown in FIG. 8, an everting force is applied to sleeve 26 by directing a stream 54 of fluid (e.g., saline) at the sleeve, e.g., using a hose 52 situated inside the intestine. (In such embodiments, capsule 20 does not necessarily comprise the coils shown in earlier figures.) In such embodiments, capsule 20 typically further comprises a flexible longitudinal element 50, such as a string or rubber cord, that may be used to withdraw the everting sleeve from the intestine, e.g., upon completion of the imaging procedure. Typically, the distal end of flexible longitudinal element 50 remains coupled to sleeve 26, while the proximal end of the flexible longitudinal element remains outside of the subject, throughout the procedure.

Flexible longitudinal element 50 may also be used in combination with earlier-described embodiments, as a fallback mechanism for withdrawing the capsule. Thus, for example, if the coils coupled to the sleeve cannot, for whatever reason, be used to withdraw the capsule, flexible longitudinal element 50 may be used instead. Alternatively, following the conclusion of the procedure, the capsule may be simply expelled by the subject during defecation.

It is noted that alternate methods for applying an everting force to sleeve 26 are also included within the scope of the present disclosure. For example, a continual everting force may be applied to sleeve 26 by a rod that is inserted into the intestine and is repeatedly pushed, partially, into the sleeve lumen.

Figure 9:
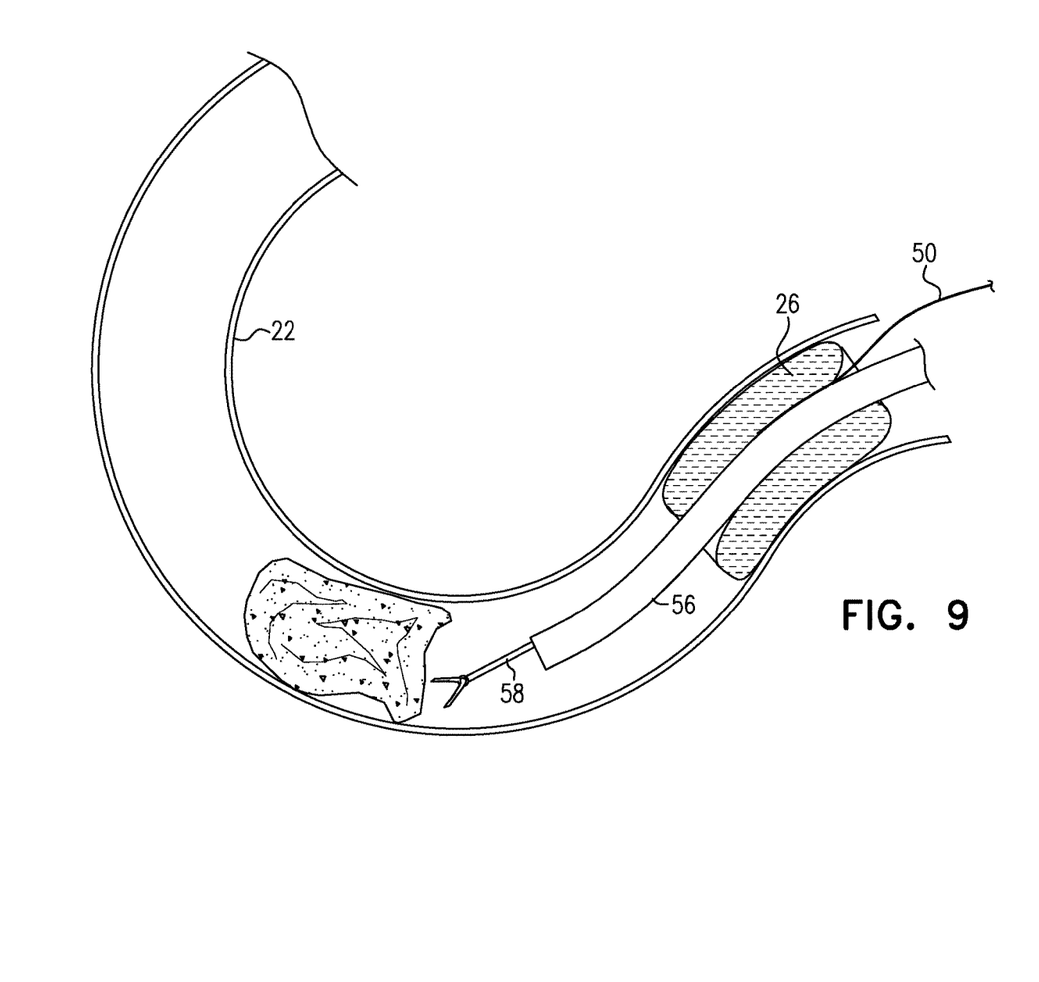
FIG. 9 is a schematic illustration of a method for advancing a tool through the lumen of an intestine, in accordance with some embodiments of the present invention.

Reference is now made to FIG. 9, which is a schematic illustration of a method for advancing a tool 56 through the lumen of intestine 22, in accordance with some embodiments of the present invention. In the embodiment shown in FIG. 9, sleeve 26 is inserted entirely into the lumen of the intestine. Subsequently, tool 56 is passed through the sleeve, i.e., through the sleeve lumen. Tool 56 may comprise, for example, a sheath, through which another tool, such as pincers 58, may be passed. Alternatively, tool 56 may comprise an endoscope, or any other suitable instrument. FIG. 9 thus illustrates that sleeve 26—due to being cyclically everting—may be used to facilitate a medical procedure, by functioning as a low-friction conduit for a tool.

Typically, when used as a conduit as in FIG. 9, there are no coils coupled to, or imaging devices contained within, sleeve 26. It is noted, however, that the embodiment shown in FIG. 9 may be combined with previously-described embodiments, such that coils on sleeve 26 may be used to move the sleeve within the intestine, and/or imaging devices within the sleeve may be used to acquire images of the intestine, before and/or after the sleeve is used as a conduit.

It will be appreciated by persons skilled in the art that the present invention is not limited to what has been particularly shown and described hereinabove. Rather, the scope of embodiments of the present invention includes both combinations and subcombinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A capsule, comprising:
    a cyclically everting sleeve shaped to define a sleeve interior;
    a fluid, configured to facilitate the everting of the sleeve, contained within the sleeve interior; and
    a plurality of electrically-conductive coils coupled to the sleeve and configured to, when at least two of the coils are magnetized, advance the capsule within a lumen by applying an everting force to the sleeve,
    wherein the coils are arranged in a plurality of rings running longitudinally along the sleeve.

2. The capsule according to claim 1, wherein the coils are radiopaque.

3. The capsule according to claim 1, further comprising one or more imaging devices contained within the sleeve interior and configured to image an interior of the lumen.

4. The capsule according to claim 1, wherein a surface of the everting sleeve is transparent.

5. The capsule according to claim 1, wherein the fluid comprises a mixture of alcohol and water.

6. The capsule according to claim 1, wherein at least one of the coils is a barrel coil.

7. The capsule according to claim 6, further comprising a ferromagnetic material disposed within a lumen of the barrel coil.

8. The capsule according to claim 1, wherein at least some of the coils overlap each other.

9. The capsule according to claim 1, wherein the coils are arranged in four or more rings distributed along a circumference of the sleeve.

10. The capsule according to claim 1, further comprising respective conducting elements attached to each coil of the coils, the respective conducting elements being configured to magnetize the coil by passing an electric current between the coil and a power source located outside of the lumen, the power source being selected from the group of power sources consisting of: a current source, and a voltage source.

11. The capsule according to claim 1, wherein a diameter of the sleeve is adjustable between a lower limit and an upper limit.

12. The capsule according to claim 11, further comprising a net configured to hold the diameter of the sleeve at the upper limit.

13. The capsule according to claim 1, further comprising one or more fiducial markers on the sleeve.

14. The capsule according to claim 1, further comprising one or more location sensors coupled to the sleeve, configured to transmit a signal indicative of a location and an orientation of the capsule.

15. A method, comprising:
inserting a capsule entirely into a lumen, the capsule including:
a cyclically everting sleeve shaped to define a sleeve interior,
a fluid, configured to facilitate the everting of the sleeve, contained within the sleeve interior, and
a plurality of electrically-conductive coils coupled to the sleeve and configured to, when at least two of the coils are magnetized, advance the capsule within the lumen by applying an everting force to the sleeve,
wherein the coils are arranged in a plurality of rings running longitudinally along the sleeve; and
advancing the capsule within the lumen, by alternately magnetizing respective subsets of the coils.

16. The method according to claim 15, wherein the capsule includes one or more imaging devices disposed within the sleeve interior, and wherein the method further comprises, while the capsule is inside the lumen, imaging an interior of the lumen, using the imaging devices.

17. The method according to claim 15, wherein alternatingly magnetizing the respective subsets of the coils comprises magnetizing two of the coils that are opposite one another such that the two coils attract one another.

18. The method according to claim 17, wherein alternatingly magnetizing the respective subsets of the coils further comprises magnetizing another two of the coils that are opposite one another such that the two coils repel one another.

19. The method according to claim 15, wherein alternatingly magnetizing the respective subsets of the coils comprises magnetizing each coil of each subset by passing an electric current along a circuit that includes at least (i) the coil, and (ii) a plurality of conducting elements running between the coil and an exterior of the lumen.

20. The method according to claim 15, wherein alternatingly magnetizing the respective subsets of the coils comprises alternatingly magnetizing the respective subsets of the coils in a predetermined order that is based on respective longitudinal positions of the coils along the sleeve.

21. The method according to claim 15, further comprising, by imaging the coils while the capsule is inside the lumen, repeatedly identifying which ones of the coils are at a longitudinal end of the sleeve, wherein alternatingly magnetizing the respective subsets of the coils comprises alternatingly magnetizing the respective subsets of the coils in response to the identifying.

22. The method according to claim 15, wherein alternatingly magnetizing the respective subsets of the coils comprises, in response to the capsule reaching a bend in the lumen, magnetizing a subset that includes coils that are located at different circumferential positions along the sleeve, relative to circumferential positions of coils belonging to the subset that was most recently magnetized.

23. The method according to claim 22, further comprising ascertaining that the capsule has reached the bend, in response to imaging one or more fiducial markers on the sleeve.

24. The method according to claim 22, wherein the capsule includes one or more location sensors, and wherein the method further comprises ascertaining that the capsule has reached the bend, in response to a signal from the sensors.

25. The method according to claim 15, wherein the lumen is a gastrointestinal lumen of a subject.

26. The method according to claim 15, further comprising, while the capsule is inside the lumen, adjusting a diameter of the sleeve in response to the capsule reaching a portion of the lumen at which a diameter of the lumen changes.

27. The method according to claim 26, wherein adjusting the diameter of the sleeve comprises increasing the diameter of the sleeve by heating the fluid.

28. The method according to claim 15, further comprising
advancing a tool through the lumen, by passing the tool through the sleeve.

* * * * *